United States Patent
Puszko et al.

[19]

[11] Patent Number: 5,902,413
[45] Date of Patent: *May 11, 1999

[54] ENDOSCOPE CLEANING SYSTEM

[75] Inventors: Grazyna Barbara Puszko; Zbigniew Puszko, both of Mount Waverley, Australia

[73] Assignee: Phillips Ormonde & Fitzpatrick, Melbourne, Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/702,519

[22] PCT Filed: Feb. 7, 1995

[86] PCT No.: PCT/AU95/00053

§ 371 Date: Aug. 27, 1996

§ 102(e) Date: Aug. 27, 1996

[87] PCT Pub. No.: WO95/21564

PCT Pub. Date: Aug. 17, 1995

[30] Foreign Application Priority Data

Feb. 28, 1994 [AU] Australia ................ PM4135

[51] Int. Cl.⁶ ................ B08B 3/04; B08B 9/00
[52] U.S. Cl. ........ 134/21; 134/22.12; 134/22.18; 134/24; 134/34; 422/33
[58] Field of Search ............ 134/18, 22.12, 134/21, 22.18, 22.11, 26, 56 R, 102.2, 166 R, 168 C, 169 C, 170, 186; 604/15, 267; 422/112, 33, 292, 295

[56] References Cited

U.S. PATENT DOCUMENTS

| | | |
|---|---|---|
| 4,281,674 | 8/1981 | Tanaka et al. ............ 134/95 |
| 4,299,244 | 11/1981 | Hirai ............ 134/102 |
| 4,525,220 | 6/1985 | Sasa et al. ............ 134/21 |
| 4,526,622 | 7/1985 | Takamura et al. ............ 134/21 |
| 4,526,623 | 7/1985 | Ishii et al. ............ 134/21 |
| 4,576,650 | 3/1986 | Yabe et al. ............ 134/22.12 |
| 4,579,597 | 4/1986 | Sasa et al. ............ 134/21 |
| 4,579,598 | 4/1986 | Sasa et al. ............ 134/22.12 |
| 4,637,378 | 1/1987 | Sasa ............ 128/4 |
| 4,667,691 | 5/1987 | Sasa ............ 134/169 C |
| 5,240,675 | 8/1993 | Wilk et al. ............ 422/22 |
| 5,274,874 | 1/1994 | Cercone et al. ............ 15/244.1 |
| 5,279,317 | 1/1994 | Bowman et al. ............ 134/166 |
| 5,279,799 | 1/1994 | Moser ............ 422/292 |
| 5,337,730 | 8/1994 | Maguire ............ 128/4 |
| 5,382,297 | 1/1995 | Valentine et al. ............ 134/15 |
| 5,425,815 | 6/1995 | Parker et al. ............ 134/26 |
| 5,494,530 | 2/1996 | Graf ............ 134/18 |
| 5,511,568 | 4/1996 | Bowman et al. ............ 134/102.2 |
| 5,514,084 | 5/1996 | Fisher ............ 604/1 |

FOREIGN PATENT DOCUMENTS

| | | |
|---|---|---|
| 3413846 A1 | 10/1984 | Germany . |
| 3413847 A1 | 10/1984 | Germany . |
| 3414962 A1 | 10/1984 | Germany . |
| 3414963 A1 | 10/1984 | Germany . |
| 3415838 A1 | 11/1984 | Germany . |
| 0089823 A2 | 9/1983 | United Kingdom . |

Primary Examiner—Harold Y. Pyon
Attorney, Agent, or Firm—Wolf, Greenfield & Sacks, P.C.

[57] ABSTRACT

A cleaning system for an endoscope is disclosed wherein the inlets of respective channels of the endoscope are connected to a suction pump through a connecting device enabling the endoscope to be cleaned by aspirating fluid through the channels under operation of the pump. The connecting device includes as passage arrangement having a plurality of first connecting ports and at least one second connecting port. The device further includes control means to control fluid flow through the passage arrangement enabling individual channels in the endoscope to be isolated from the suction.

15 Claims, 3 Drawing Sheets

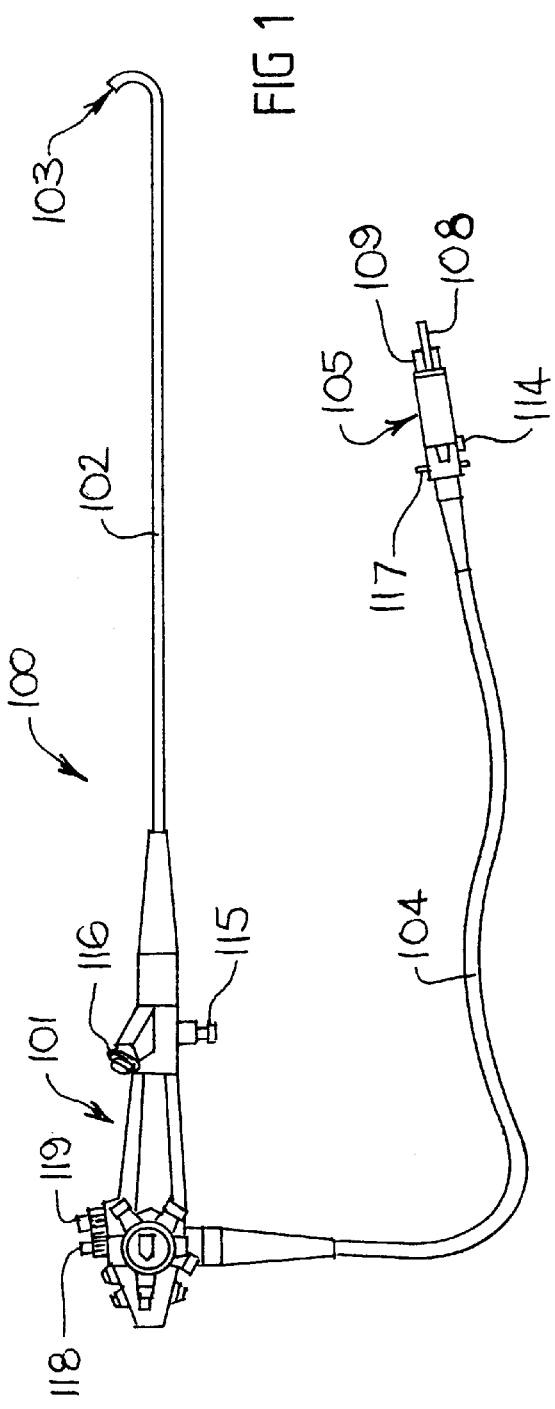
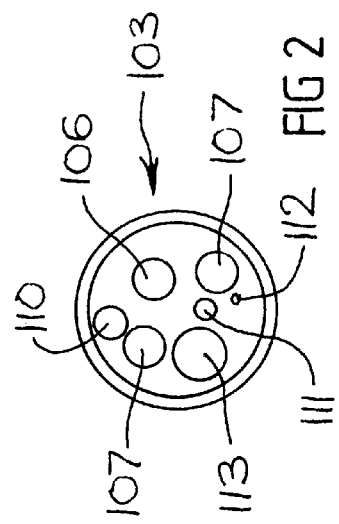

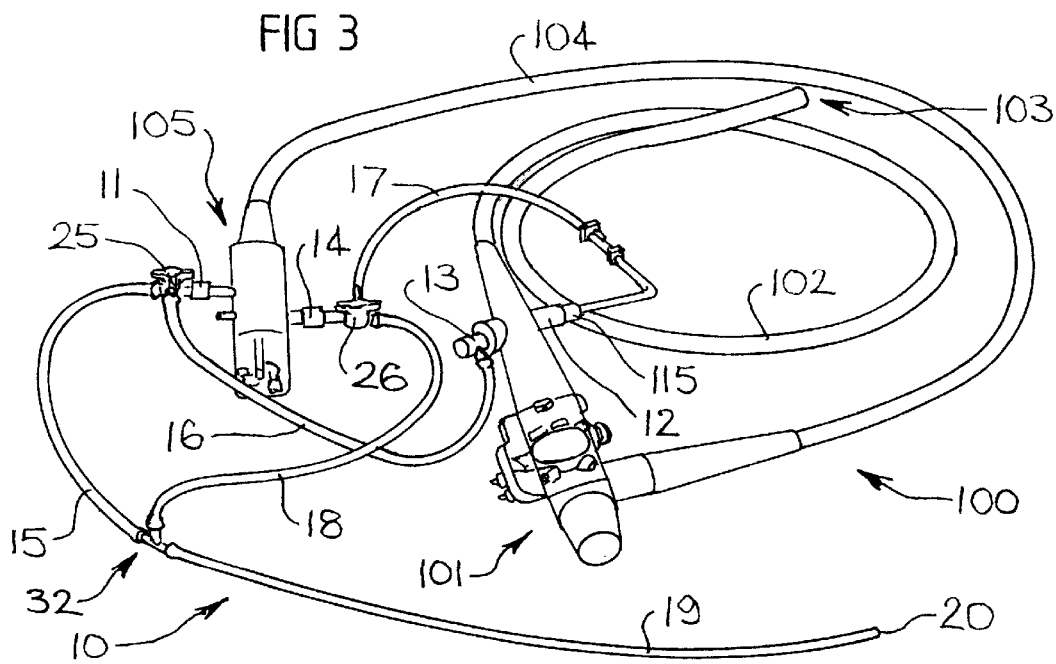

ENDOSCOPE CLEANING SYSTEM

This application is a 371 of PCT/AU95/00053 filed on Feb. 7, 1995.

BACKGROUND OF THE INVENTION

The present invention relates to a method of and apparatus for cleaning an endoscope. The invention is suitable for use on all types of endoscopes including both fiberscopes and video endoscopes and has particular application in the cleaning of the channels within the endoscope after use, and is herein described in this context. However, it should be appreciated that the invention has broader application and is not limited to this particular use.

Endoscopes are widely used in medical diagnosis, therapy and research. A typical endoscope incorporates a control section, from which an insertion tube and universal cord extend. The insertion tube incorporates a distal end which includes an objective lens and light guides, and the universal cord incorporates a connecting head at its outer end through which the light source and power are supplied to the endoscope.

A plurality of channels extend through the endoscope to the distal end. These channels, which include a working channel and water and air channels, allow access to enable various functions to be provided at the distal end. The working channel enables forceps and other instruments to be used at the distal end and is also usually connected to a source of suction to provide suction at the distal end. The water and air channels are primarily provided to clean the objective lens. Other channels may also be incorporated including auxiliary water channels to provide irrigation at the inspection site, auxiliary instrument channels and $CO_2$ insufflation channels.

Each of these channels incorporates an inlet port. Usually the instrument channel inlet port is located at the control section with the inlet ports for the other channels located at the connector head, though this may vary with different types of endoscopes.

To maintain adequate performance of the endoscope and to stop cross-infection, it is necessary that the endoscope is thoroughly cleaned after each use, and in cleaning the endoscope it is necessary that each individual channel is thoroughly cleaned.

In the past a method of cleaning the endoscope includes applying pressure, usually via a syringe, at each inlet port of the channels to flush fluid through the individual channels to the distal end. While this procedure is adequate, this process is time consuming and labour intensive.

SUMMARY OF THE INVENTION

An aim of the present invention is to provide a more effective procedure for cleaning an endoscope and in particular for cleaning the channels of the endoscope.

Accordingly, in one aspect, the present invention relates to a method of cleaning an endoscope having a plurality of channels communicating with a distal end of the endoscope, the method including the steps of:
(i) locating the distal end of the endoscope in a fluid; and
(ii) causing the fluid to flow from the distal end of the endoscope through the respective channels of the endoscope.

In the specification the term "cleaning" is defined to include within its scope any or all of the processed of washing, disinfecting and sterilising, whether these processes are done separately or as part of an overall procedure.

A particular advantage of this method is that as many of the endoscope channels incorporate a constricted outlet at their distal end, the likelihood of solid matter becoming lodged in the channels during the cleaning process according to the above method is reduced as compared to prior art methods. This is particularly the case with the air and water channels where the outlets at the distal end are usually designed to provide a pressurised or directed flow.

In a preferred method, fluid is aspirated through the respective channels and each of the inlet ports of the channels to be cleaned are connected to a source of suction through connecting means. In a particularly preferred arrangement, the respective inlet ports are all connected to a single source of suction, thereby enabling all the channels to be cleaned in a single processing step.

In a second aspect, the present invention provides a method of cleaning an endoscope having a plurality of channels, each channel having an inlet and an outlet, the method including the steps of:
(i) providing connecting means having a plurality of first connecting ports;
(ii) connecting each of the inlets of the endoscope to a respective one of the first connecting ports;
(iii) causing a fluid to flow through the connecting means to enable cleaning of the respective channels of the endoscope.

Preferably, the connecting means includes at least one second connecting port, and each of the first connecting ports is able to be in fluid communication with the or each second connecting port. In this way, a single source of suction may be applied to one of the second connecting ports to aspirate fluid through the respective channels of the endoscope. Furthermore, if required, one of the second connecting ports may be connected to a fluid source enabling fluid from the single fluid source to flow into each of the respective channels.

Preferably fluid flow in the channels is regulated by controlling the flow of fluid through the connecting means.

Preferably the connecting means includes a plurality of conduits each incorporating viewing means to enable visual inspection of the fluid which passes through the individual channels.

While any suitable source of suction may be used, the method of the present invention may conveniently employ a suction machine which is used in conjunction with the endoscope. With this arrangement, the method may be easily introduced into existing procedures without requiring expensive capital outlay for equipment.

In a preferred method, all the channels are connected via conduits to a single source of suction to enable fluid to be aspirated through the respective channels in a single step. Furthermore, typically a variety of fluids are aspirated through the channels in cleaning of the endoscope including water, cleaning solution, air, and disinfectant. Furthermore, these processing steps may be undertaken manually by changing the fluid bath in which the distal end or complete endoscope is located, or alternatively may be undertaken in an automated process, wherein the distal end or complete endoscope is placed in a fluid bath through which various fluids are introduced and removed whilst the aspiration of fluid in the channels is controlled by automatically controlling suction through the respective channels. Furthermore, as part of the cleaning process, the connecting means may also be connected to a single fluid source enabling fluid from this single source to flow into each of the respective channels.

In a third aspect, the present invention relates to a connecting device for use with an endoscope incorporating a plurality of channels each having a respective inlet, the connecting device including passage means having a plurality of first connecting ports each being adapted to be secured to a respective one of the inlets of the endoscope, and at least one second connecting port, the passage means being arranged so that each of the first connecting ports is able to be in fluid communication with the or each second connecting port. In use the connecting device may be used in applying positive pressure or suction to the channels of the endoscope by connecting at least one of the second connecting ports to a pump.

Preferably the connecting device includes control means operable to inhibit fluid communication between at least one of the first connecting ports and at least one of the second connecting ports.

Preferably the passage means comprises a plurality of conduits. Preferably the conduits incorporate viewing means enabling monitoring of the fluid in the respective conduits.

In a preferred arrangement, the conduits are substantially transparent, and are typically formed from a polymer tubing.

Preferably the control means is in the form of valving means arranged to prevent fluid flow in at least some of the conduits. Preferable the valving means comprises stopcocks.

In a fourth aspect, the present invention relates to a cleaning apparatus for an endoscope incorporating a plurality of internal channels each having an outlet located at the distal end of the endoscope and an inlet, the apparatus including a connecting device, a pump and a fluid bath, the connecting device connecting in fluid communication the internal channels to the pump and wherein the distal end of the endoscope is located in fluid communication with the fluid bath, the apparatus being arranged such that on operation of the pump, fluid from the bath is caused to flow from the distal end through the channels of the endoscope.

Preferably, the endoscope includes at least one air and/or water channel and wherein the connecting device connects the air and/or water channel to the pump to cause fluid flow from the distal end through the channels on operation of the pump.

Preferably, the connecting device is connected to the respective inlets of the internal channels and the pump is a suction pump such that fluid from the fluid bath is aspirated from the distal end through the channels of the endoscope.

Preferably, the cleaning apparatus provides control means operable to regulate the flow of fluid in at least one of the channels of the endoscope.

The cleaning apparatus according to this aspect of the invention may be controlled through an automated process and include second control means arranged to regulate the flow of fluid in the fluid bath.

The cleaning apparatus may further incorporate a housing containing the endoscope and fluid bath. The housing may be sealed enabling the temperature within the housing to be controlled. The source of suction may be incorporated in the housing or an eternal source of suction may be used which is in communication with the connecting device through a conduit which extends through the housing.

BRIEF DESCRIPTION OF THE DRAWINGS

It will be convenient to hereafter describe the invention in greater detail with reference to the accompanying drawings. The particularity of those drawings and the associated description is not to be understood as superseding the generality of the preceding broad description of the inventive concept.

In the drawings:

FIG. 1 illustrates a schematic view of a video endoscope;

FIG. 2 illustrates a detailed view to an enlarged scale of the distal end of the endoscope of FIG. 1;

FIG. 3 illustrates a connecting device according to a first embodiment of the present invention;

FIGS. 3A and 3B are detailed views to an enlarged scale of coupling elements of the connecting device of FIG. 3.

FIG. 5 illustrates the connecting device according to a second embodiment of the present invention.

DETAILED DESCRIPTION

Figure 4:
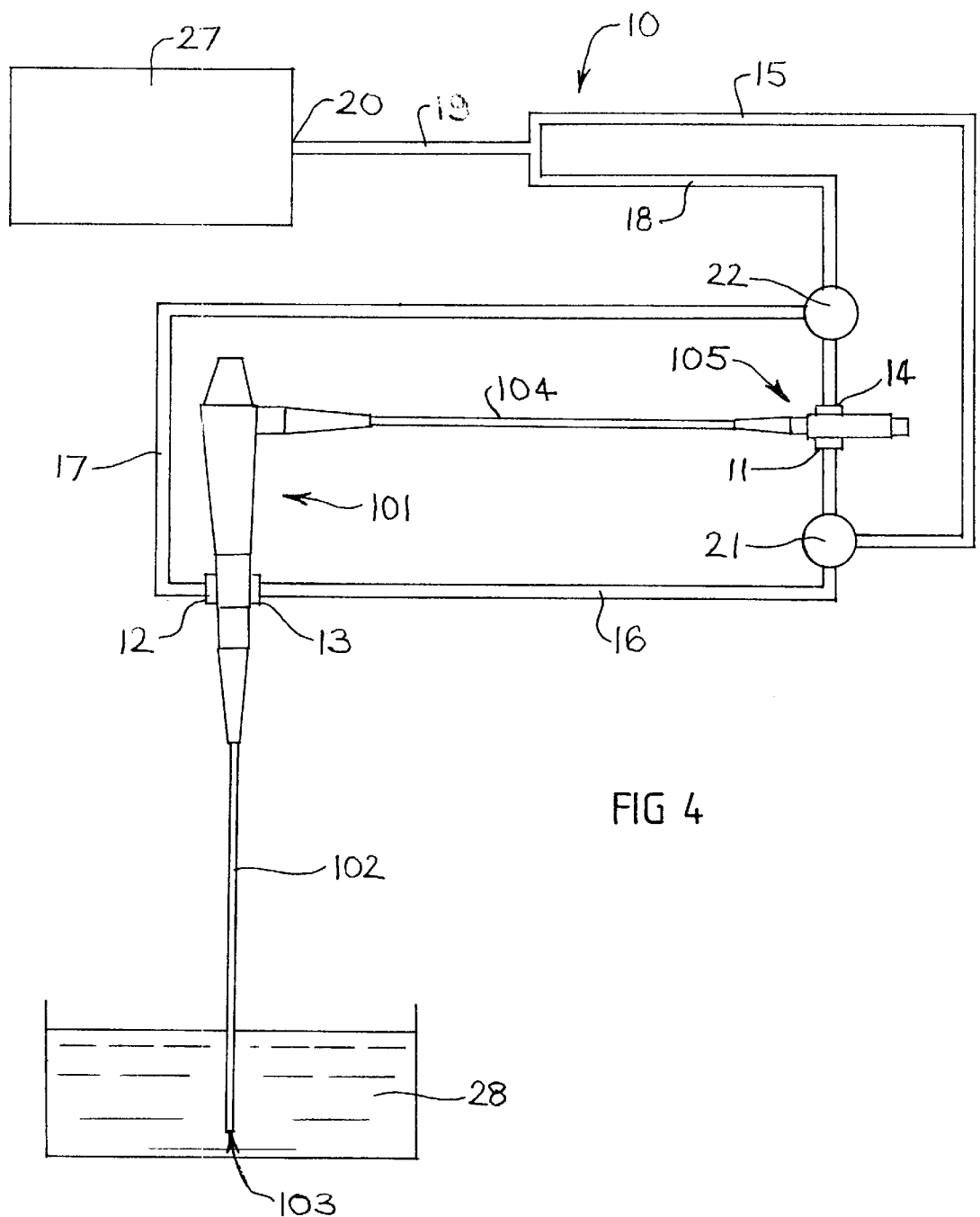
FIG. 4 illustrates the connecting device of FIG. 3 connected to the video endoscope of FIG. 1.

FIGS. 1 and 2 illustrate a video endoscope 100. The endoscope includes a control section 101, an insertion tube 102 extending from the control section 101 to a distal end 103 and a universal cord 104 also extending from the control section 101 and having a connector section 105 at its outer end. The distal end 103 of the endoscope 100 includes an objective lens 106 and light guides 107. The connector section 105 incorporates a light guide terminal 108 for connection to a light source (not shown) and an electrical terminal 109 to supply power to the endoscope 100.

The endoscope incorporates a plurality of internal channels, each extending to the distal end of the endoscope from either the control section 101 or the connector section 105. These channels allow various functions to be performed at the distal end 103.

In the illustrated arrangement, the video endoscope 100 includes an air channel having an outlet 110 at the distal end 103 which incorporates an air feeding nozzle to direct pressurised air across the objective lens 106. The air feeding nozzle also provides distension of the cavity being examined.

A first water channel is provided which has an outlet 111 at the distal end. This outlet incorporates a water feeding nozzle which is arranged to direct pressurised water across the objective lens to clear debris from the lens. A water jet channel is also provided which has an outlet 112 at the distal end which incorporates a water jet nozzle which is arranged to direct pressurised spray at the surface under examination.

The endoscope 100 incorporates a working channel which includes an outlet 113 at the distal end. The working channel enables instruments such as forceps to be introduced into the cavity being examined. On addition the working channel is connected to a source of suction to provide suction at the distal end 103. Other channels may be incorporated into the endoscope. For example in a fiberoptic colonscope, a $CO_2$ insufflation channel or an auxiliary instrument channel may be included.

Each of the channels incorporates an inlet port at various locations on the endoscope 100. In the illustrated arrangement, the first air channel and the water channel have a common inlet port 114 located at the connector section 105. The water jet channel incorporates an inlet port 115 at the control section 101 whereas the working channel incorporates one inlet 116 in the control section 101 for the introduction of an instrument and a second inlet port in the form of a suction nipple 117 on the connector section 105.

FIG. 3 illustrates a connecting device 10 for the endoscope 100. The device 10 incorporates passage means 32 having a plurality of first connecting ports (11, 12, 13 and 14), and a second connecting port 20. The passage 32 means is in the form of a plurality of conduits (15, 16, 17, 18 and 19) which are interconnected such that each of the connecting ports is able to be in fluid communication with the second connecting port 20. Furthermore, the conduits are substantially transparent to allow visual inspection of fluid flow in the conduits. It should be appreciated that the passage means may take other forms. For example, the passage means could comprise a single conduit having the first and second connecting means spaced thereon. However, for ease of operation of the device 10 it is preferable to have the device formed from a plurality of conduits.

Each connecting port is adapted to be connected to a respective inlet port of the endoscope 100. In particular, connecting port 11 is adapted to be connected to the combined water/air inlet 114, the connecting port 12 is adapted to be connected to the water jet channel inlet port 115, the connecting port 13 is adapted to be connected to the working channel inlet port 116 located on the control section 101 and the connecting port 14 is adapted to be connected to the suction nipple 117. It should be appreciated that if the endoscope incorporated additional channels, the connecting device 10 could be modified to connect these additional inlet ports to additional first connecting ports.

Each of the first connecting ports includes a coupling element enabling each connecting port to sealingly engage with a respective one of the inlets. As different models of endoscope include different inlet configurations, the coupling elements vary depending on the model of endoscope and the preference of the end user. In the illustrated arrangement, a slip lock 21, 22 and 23 is incorporated on connecting ports 11, 12 and 13 and a luer lock 24 is incorporated on the air/water connecting port 14.

FIGS. 3A and 3B show detailed views of the luer lock 24 and the slip lock 21 respectively. As can be seen, the luer lock 24 includes an inner tube 33 which is frustoconical and which is adapted to be located within the air/water connecting port. The tapered outer surface of the tube 33 ensures a friction fit between the coupling element and the port. A sleeve 34 includes a thread 35 on its inner surface and is adapted to engage an outer surface of the port to secure the luer lock 24 to the port. The slip lock 21 is similar to the luer lock 24 except that it does not provide the sleeve 32 and maintains engagement with its respective port merely through the frictional fit.

In the illustrated arrangement, the luer lock 24 forms part of a junction connection which incorporates a three way stopcock 26 which forms part of a control arrangement. The control arrangement is operable to regulate fluid flow between the second connecting port 20 to each of the first connecting ports (11, 12, 13, 14). In this way, when the first connecting ports are connected to the inlet ports of the endoscope, all of the respective channels of the endoscope may be in fluid communication with the second connecting port 20 of the connecting device 10 or any one channel or any combination of channels may be isolated to be the only channel or channels in communication with the second connecting port 20.

In the illustrated arrangement, the control arrangement includes two three-way stopcocks 25 and 26 which are located adjacent first connecting ports 11 and 14.

To assist in connection of the connecting device 10 to the endoscope 100, the device 10 is colour coded, typically through heat-shrink bandages located on the conduits adjacent the stopcocks 25 and 26 or by making the conduits in different colours.

Valves 118, 119 on the endoscope 100 are used to control the air/water flow and suction at the distal end during operation of the endoscope. In after use cleaning of the endoscope 100 these valves are typically replaced by caps or other adaptors (not shown) in accordance with the manufacturer's instructions.

FIG. 4 illustrates schematically the connecting device 10 connected to the endoscope 100 and a source of suction 27 to provide for cleaning of the channels within the endoscope 100. As part of the cleaning arrangement, the distal end 103 of the endoscope 100 is located in a fluid bath 28. Whilst any suitable suction machine may be used, it is envisaged that for convenience, the suction machine associated with the endoscope 100 is used. A typical suction machine of this type is a low suction digital intermittent pump such as that manufactured by Clements Medical Equipment. However, it should be appreciated that any suitable suction pump may be used.

As clearly illustrated in FIG. 4, the connecting device 10 interconnects each of the inlet ports of the endoscope 100 to the suction pump 27. By applying suction to the second connecting port 20 from the pump 27, fluid from the fluid bath 28 is aspirated through any or all of the channels in the endoscope 100, with the choice of channels through which the fluid is aspirated being dependent on the setting of the valves 25 and 26.

FIG. 5 illustrates a further embodiment of the connecting device which is adapted to be used on a video gastroscope which does not include a second water jet channel or $CO_2$ insufflation channel.

This embodiment is similar to the first embodiment and like features have been given like references. A primary difference in this embodiment is that the device 10 does not include the conduit 17 or the stopcock 26. This arrangement is preferred for use on gastroscopes as there is only one stopcock 25 controlling fluid flow through the inlets which simplifies operation of the device. However, by omitting the stopcock 26 there is not a valve to control fluid flow in the air/water channel. This does not unduly effect the operation of the device as the air/water channel is much smaller than the working channel and therefore the amount of fluid flowing through the air/water channel compared to the working channel is small. Accordingly, while it is desirable to be able to shut off the suction channel to ensure adequate cleaning of the air/water channel, it is not as important to cut off the air/water channel to ensure adequate cleaning of the suction channel. Nevertheless, if desired, the air/water channel may be shut off be merely kinking the conduit 18 to block fluid flow.

It should be appreciated that the embodiment illustrated in FIGS. 3 and 4 can also be used with the video gastroscope where there is no water jet channel or $CO_2$ insufflation channel. In this arrangement the connecting port 12 would be free and to compensate for this free connecting port, the stopcock 26 would be set to ensure that the conduit 17 is shut off.

Furthermore in this embodiment, an additional conduit 29 is provided adjacent the second connecting port 20 which provides a further second connecting port 30. The device also includes a further three way stopcock 31 which is operable to control fluid flow through the conduit 29 and through the connecting port 30.

The provision of a further second connecting port is designed primarily to provide an alternative arrangement during disinfection of the channels which will be discussed in more detail later. However, by having the two second connecting ports 20, 30 further flexibility is added to the use of the device 10. For example, one of the second connecting ports can be connected to a fluid source (not shown) whilst the other is connected to a source of suction, thereby enabling through operation of the stopcock 31, a cleaning process which alternates between aspirating of fluid from the distal end of the endoscope to fluid flow from the fluid source under positive pressure. Alternatively, if the endoscope has an additional inlet, one of the second connecting devices can be connected to this further inlet channel and the other second connecting port connected to the source of suction. Furthermore, it is to be appreciated that this arrangement may also be incorporated into the embodiment of the device 10 as illustrated in FIGS. 3 and 4.

The process of cleaning the channels of the endoscope 100 using the connecting device 10 may easily be incorporated into the existing procedures currently employed in after-use cleaning, disinfecting and sterilisation of endoscopes. By way of example, this process of cleaning may be used as follows.

After use, the endoscope is wiped down, and the air/water valve button is depressed to flush refluxed blood or other material out of the air/water channel under positive pressure. The distal end of the endoscope may also be placed in a fluid bath of solution and the suction valve closed to aspirate solution through the suction channel.

The valves 118 and 119 are then removed and the working channel is cleaned by inserting a cleaning brush. Due to the constricted outlets at the distal end, it is not possible to brush out the air/water channel. The valves 118 and 119 are replaced by air/water and suction channel caps and the connecting device 10 is connected to the respective inlet of the endoscope as described above.

The endoscope is then immersed fully in a fluid bath containing a cleaning solution such as detergent and one of the second connecting ports (20 or if available 30) is connected to the suction pump 27. The suction pump is operated and the cleaning solution is aspirated through the channels of the endoscope and the valve 25 (and if available, valve 26) is manipulated to isolate various channels as required. Fluid which has passed through the channel is monitored by visual inspection of fluid flow through the conduits of the connecting device 10. After this initial cleaning, the distal end of the endoscope is then removed from the bath and air is aspirated through the channels under the operation of the suction pump 27 to remove the cleaning solution from the channels.

The endoscope is then fully flushed with clean water by being immersed in a clean water bath with the suction pump 27 operated to aspirate the water through the channels to thereby flush out the channels. The distal end of the endoscope is then removed from the bath and air is aspirated through the channels under the operation of the suction pump 27 to remove the water from the channels.

The endoscope is then disinfected. In one arrangement, the endoscope is immersed in a bath of disinfectant solution and the disinfectant is aspirated into the channels under the operation of suction pump 27, and remains in the channels for the required time to ensure adequate disinfection. Alternatively, the second connecting port connected to the pump 27 is cut off from the suction pump 27 (which if available can be achieved through operation of stopcock 31) and one of the second connecting ports (20 or if available 30) is placed in fluid communication to a source of disinfectant which is forced under positive pressure into the channels. In an another arrangement, the conduit 29 is placed in a fluid source containing the disinfectant such that the second connecting port 30 is in fluid communication with the fluid source. A syringe is located at the other second connecting port 20. The stopcock 31 is set to shutoff the conduit 19 and fluid is drawn up into the syringe. The stopcock is then moved to shutoff the fluid source, and the fluid in the syringe is then pushed through each of the channels. Again, inspection of the conduits ensure that each of the channels incorporates the disinfectant. Furthermore, if required selected channels may be isolated to ensure that each of the channels is filled with disinfectant.

After the channels have been fully disinfected, the disinfectant is removed from the channels either by removing the distal end of the endoscope from the disinfectant bath and aspirating air through the channels under the suction pump 27 or alternatively, the second connecting ports are removed from the fluid source and air is pumped through the channels by the positive pressure source.

After disinfection, the endoscope is flushed with clean water by aspirating the water through all the channels under the suction pump 27 or by connecting one of the second connecting ports to a water tap and flushing water under positive pressure through the channels. To ensure adequate rinsing it is recommended that approximately 30 liters of water should be flushed through the channels.

The channels are dried by aspirating air through the channels under the suction pump 27 and then the tip of the distal end 103 is inserted in a solution of 70% alcohol which is aspirated through the channels under the suction pump 27. The channels are then dried again under the action of the suction pump 27. Typically air would be aspirated through the channels for 10 minutes to ensure that the channels are completely dry.

In standard procedure, the endoscope undergoes a leak test procedure prior to immersion and the accessories, including the air/water valve, the biopsy valve, and instruments, are all cleaned separately from the endoscope.

An advantage of using the connecting device 10 is that after use cleaning time may be reduced substantially as the channels can be cleaned simultaneously, rather than individually. Furthermore, the endoscope is more thoroughly cleaned and dried as the device enables much greater quantities of fluid flow through the channels as compared to prior art techniques using syringes. The cleaning process is also much less labour intensive, and the person cleaning the endoscope has less contact with the disinfectant and other cleaning solutions.

A further advantage of the connecting device 10 is that by aspirating fluid back from the distal end, there is less chance of blocking the channels as the solid matter is not forced through any constricted outlet. This is particularly the case with the air/water channels.

A further advantage of using the connecting device 10 is that it facilitates the automation of the cleaning process. In particular, flow through the channels can be regulated by the control of the valves 25 and 26, the type of fluid which is passed through the channels can be regulated by changing the solution in the fluid bath 28, and the rate of suction through the channels can be regulated by the pump 27 and also through the valve 31 if available. All these steps may be done through an automated process. Furthermore, as the fluid may flow through a single connecting port 20, the removal or recycling of the fluid can be easily controlled.

Finally, it is to be appreciated that various modifications and/or additions may be made to the apparatus and method as disclosed herein without departing from the ambit of the present invention herein disclosed.

What is claimed is:

1. A method of cleaning an endoscope having a plurality of individual internal channels, each individual internal channel having an inlet and an outlet, the method comprising:

(i) providing connecting means having a plurality of first connecting ports and at least one second connecting port, each of the first connecting ports being able to be in fluid communication with the at least one second connecting port, the connecting means further including control means operable to inhibit fluid communication between different parts of the connecting device so as to selectively inhibit fluid communication between the at least one second connecting port and respective ones of the first connecting ports;

(ii) connecting each of the inlets of the endoscope to a respective one of the first connecting ports;

(iii) causing fluid to flow through the endoscope and the connecting means between the outlet of the respective internal channels and the at least one second connecting port; and (iv) cleaning the respective individual internal channels of the endoscope by operating the control means to establish different fluid paths in the connecting means by selectively inhibiting fluid communication between different parts of the connecting means to thereby regulate the flow of fluid in the respective internal channels of the endoscope.

2. The method according to claim 1, further comprising:

(i) locating the outlets of the channels in fluid; and (ii) applying suction to at least one of the second connecting ports to aspirate said fluid through the respective individual internal channels of the endoscope.

3. The method according to claim 1, further comprising:

(i) connecting at least one of the second connecting ports to a fluid source; and (ii) causing fluid from said fluid source to flow through the respective individual internal channels of the endoscope.

4. The method according to claim 1 wherein a plurality of fluids are caused to flow through the respective individual internal channels of the endoscope.

5. The method according to claim 4 wherein the fluid caused to flow through the respective individual channels is selected from the group comprising:

water, cleaning solution, air and disinfectant.

6. A connecting device to interconnect an endoscope to a pump, the endoscope incorporating a plurality of individual internal channels each having a respective inlet, the connecting device including passage means formed from a plurality of interconnected individual conduits, first connecting ports located at respective ones of the individual conduits each being secured to a respective one of each of the inlets of the endoscope, and at least one second connecting port connected to the pump, the at least one second connecting port being formed in said passage means and arranged in fluid communication with each of the first connecting ports, the connecting device further including control means operable to inhibit fluid communication between selective ones of the plurality of conduits so as to selectively inhibit fluid communication between the at least one second connecting port and respective ones of the first connecting ports to establish different fluid paths in the connecting device to thereby regulate the flow of fluid in the individual internal channels of the endoscope under operation of the pump.

7. The connecting device according to claim 6, wherein the passage means include viewing means enabling visual inspection of fluid in the passage means.

8. The connecting device according to claim 6, further including coupling elements located at the respective first connecting ports, each coupling element enabling the first connecting port to which it is associated with to be sealingly connected to a respective one of the inlets of the endoscope.

9. The connecting device according to claim 6, wherein the passage means is formed from elastomer tubing.

10. The connecting device according to claim 6, wherein the device includes a plurality of second connecting ports.

11. The connecting device according to claim 6 wherein the control means includes at least one valve operable to prevent fluid flow through a selected one conduit of the plurality of conduits.

12. The connecting device according to claim 11, wherein the plurality of conduits interconnect at a junction and wherein said valve is located at the junction and is operable to control fluid flow through the respective individual conduits intersecting at said junction.

13. The connecting device according to claim 11, wherein the valve comprises a stopcock.

14. A cleaning apparatus for an endoscope incorporating a plurality of individual internal channels each having an outlet located at a distal end of the endoscope, and an inlet, the cleaning apparatus comprising:

a connecting device, a pump, a fluid bath, the connecting device connecting in fluid communication the individual internal channels to the pump, wherein the distal end of the endoscope is located in fluid communication with the fluid bath, and wherein the connecting device comprises:

passage means formed from a plurality of interconnected individual conduits, first connecting ports located at respective ones of the individual conduits each being secured to a respective one of the inlets of the endoscope, and at least one second connecting port secured to the pump the at least one second connecting port being formed in said passage means and arranged in fluid communication with each of the first connecting ports, and control means operable to inhibit fluid communication between selective ones of the plurality of conduits so as to selectively inhibit fluid communication between the at least one second connecting port and respective ones of the first connecting port, the cleaning apparatus being arranged such that on operation of the pump, fluid from the bath is caused to flow from the distal end through the individual internal channels of the endoscope, the control means being operable to establish different fluid flow paths in the connecting means by selectively inhibiting fluid communication between different parts of the connecting device so as to regulate the flow of fluid in the individual internal channels of the endoscope.

15. The cleaning apparatus according to claim 14, wherein the connecting device is connected to the respective inlets of the individual internal channels, and wherein the pump is a suction pump such that fluid from the fluid bath is aspirated from the distal end through the individual internal channels of the endoscope.

* * * * *

UNITED STATES PATENT AND TRADEMARK OFFICE
CERTIFICATE OF CORRECTION

PATENT NO. : 5,902,413
DATED : May 11, 1999
INVENTOR(S) : Puszko et al.

It is certified that error appears in the above-identified patent and that said Letters Patent is hereby corrected as shown below:

On cover page, in item [75], the Assignee, "PHILLIPS ORMONDE & FITZPATRICK" should be --PSK CONNECTORS PTY. LTD., Victoria Australia--

Signed and Sealed this

Twenty-first Day of March, 2000

Attest:

Q. TODD DICKINSON

Attesting Officer

Commissioner of Patents and Trademarks